US009433519B2

(12) United States Patent
Osypka

(10) Patent No.: US 9,433,519 B2
(45) Date of Patent: Sep. 6, 2016

(54) HIGHLY FLEXIBLE STENT HAVING A PREDETERMINED BREAKING POINT

(71) Applicant: Peter Osypka, Grenzach-Wyhlen (DE)

(72) Inventor: Peter Osypka, Grenzach-Wyhlen (DE)

( * ) Notice: Subject to any disclaimer, the term of this patent is extended or adjusted under 35 U.S.C. 154(b) by 61 days.

(21) Appl. No.: 14/379,826

(22) PCT Filed: Feb. 7, 2013

(86) PCT No.: PCT/DE2013/000067
§ 371 (c)(1),
(2) Date: Aug. 20, 2014

(87) PCT Pub. No.: WO2013/131501
PCT Pub. Date: Sep. 12, 2013

(65) Prior Publication Data
US 2015/0366685 A1 Dec. 24, 2015

(30) Foreign Application Priority Data
Mar. 3, 2012 (DE) .................. 20 2012 002 340 U

(51) Int. Cl.
*A61F 2/915* (2013.01)
*A61F 2/89* (2013.01)
*A61F 2/82* (2013.01)

(52) U.S. Cl.
CPC .................. *A61F 2/915* (2013.01); *A61F 2/89* (2013.01); *A61F 2002/825* (2013.01); *A61F 2002/9155* (2013.01); *A61F 2250/0067* (2013.01); *A61F 2250/0071* (2013.01)

(58) Field of Classification Search
CPC .............. A61F 2/91; A61F 2/89; A61F 2/90; A61F 2002/825; A61F 2/915; A61F 2002/9155; A61F 2250/0067
USPC ....................................................... 623/1.16
See application file for complete search history.

(56) References Cited

U.S. PATENT DOCUMENTS

| 5,591,223 A | 1/1997 | Lock et al. |
| 2002/0128706 A1 | 9/2002 | Osypka |

(Continued)

FOREIGN PATENT DOCUMENTS

| DE | 10103000 A1 | 8/2002 |
| DE | 10105160 A1 | 8/2002 |

(Continued)

OTHER PUBLICATIONS

International Search Report issued May 7, 2013 in connection with PCT/DE2013/000067.

*Primary Examiner* — Christian Sevilla
*Assistant Examiner* — Seema Mathew
(74) *Attorney, Agent, or Firm* — Locke Lord LLp; Scott D. Wofsy; Daniel J. Fiorello

(57) ABSTRACT

The invention relates to an implantable stent which can be used in the region of an arterial constriction said region being expandable by a balloon catheter. The stent is expandable and can be widened in a radial direction by virtue of the fact that the wall of the stent is formed at least in sections thereof from permanently deformable metal struts, whereby the stent consists of more than one tubular segment (10), wherein the segment (10) consist of metal struts (2) and wherein in each case two adjacent segments (10) are connected to each other by at least one pair of eyelets (6) and (7), where the eyelets (6) and (7) are connected to each other by being embedded in plastic and in this manner the segments (10) are held together, and where at least one of the metal struts (2) has a predetermined breaking point in the middle section of the segment (40), which predetermined breaking point is produced as a result of the fact that two strut sections (3) and (4) have eyelets (11), (12) respectively, which are connected to each other by being embedded in plastic, so that when they exceed a defined radial expansion, the metal struts (2) open as a result of the predetermined breaking point.

3 Claims, 2 Drawing Sheets

(56) References Cited

U.S. PATENT DOCUMENTS

| | | | | |
|---|---|---|---|---|
| 2006/0069424 A1* | 3/2006 | Acosta | | A61F 2/91 623/1.12 |
| 2006/0173529 A1* | 8/2006 | Blank | | A61F 2/91 623/1.16 |
| 2007/0021828 A1* | 1/2007 | Krolik | | A61F 2/91 623/1.31 |
| 2007/0270932 A1* | 11/2007 | Headley | | A61F 2/95 623/1.11 |
| 2011/0060401 A1* | 3/2011 | Hoerstrup | | A61F 2/2418 623/1.16 |
| 2011/0319982 A1* | 12/2011 | Bayer | | A61L 31/022 623/1.34 |
| 2012/0303112 A1* | 11/2012 | Armstrong | | A61F 2/07 623/1.16 |

FOREIGN PATENT DOCUMENTS

| | | | | |
|---|---|---|---|---|
| DE | 102004027108 A1 | | 12/2005 | |
| DE | 102008045039 A1 | | 3/2010 | |
| DE | 202011003403 U1 | | 5/2011 | |
| EP | 1563806 A1 | | 8/2005 | |
| EP | 1563806 A1 | * | 8/2005 | ........ A61F 2/91 |
| EP | 1958598 A1 | | 8/2008 | |
| WO | WO-2007013102 A1 | | 2/2007 | |

* cited by examiner

HIGHLY FLEXIBLE STENT HAVING A PREDETERMINED BREAKING POINT

The invention relates to an implantable stent, which can be used in the region of an arterial constriction said region being expandable by a balloon catheter. The stent is expandable and can be widened in a radial direction by virtue of the fact that the wall of the stent is formed at least in sections thereof from permanently deformable metal struts. If the metal struts exceed a certain radial expansion they will open as a result of an existing pre-determined breaking point.

Stents of this kind are required especially in the treatment of pulmonary stenosis among children.

The possibilities of expanding in a radial direction are limited depending on the stent model. Especially in such cases in which expansion in several steps is desired, as it is the case with children suffering from pulmonary stenosis, difficulties may occur. If immediate surgery is avoided and a normal stent is implanted in these babies, this will itself cause stenosis after a few years of growing vessels.

Stents are already known in various forms.

DE 101 05 160 B4 corresponding to US200212807 describes an expandable stent. The stent is continuously broken along the one long side. Eyelets are provided on both sides of the break, which are held together by an absorbable thread, so that the stent is initially sealed. Once the thread is removed or dissolved the stent can open, which means further expansion of the stent is possible.

DE 10 2004 027 108 B4 describes a stent, which is expandable in two steps. During an initial extension step a wall section is blocked from being extended by a fixture made of biodegradable material. After the fixture is dissolved, further extension is possible.

DE 101 03 000 A1 describes a radially expandable stent. The grid-shaped stent consists of at least two tubular sections having a zigzag structure, said sections being connected by a resorbable thread connection.

DE 10 2008 045 039 A1 describes a stent having a flexible wall. A wall region is formed by two spirals lying into one another. Thus, the stent is expandable in a radial direction.

U.S. Pat. No. 5,591,223 describes a radially expandable stent comprising an elongated sleeve member in which the radially outward expansion of the sleeve member is initially limited by connecting strips which are operatively connected to the sleeve member. The connecting strips are selectively removable to allow further radial outward expansion.

The German utility patent 202011003403 describes a stent consisting of tubular segments, where the segments are made of metal struts, and where at least one of the metal struts has a predetermined breaking point within the segment, which is formed by a slotted eyelet.

An important requirement is a high degree of flexibility between the individual segments combined with the possibility that the wall of the stent is expandable. Especially with infants, excessive rigidity of the stent may lead to a perforation of the vessel. As children grow their vessels are also enlarged compared with when the implantation was carried out, so that the stent implanted in the young child has to be replaced by a larger one.

In addition, the expandable stents described above may cause problems due to their closed metallic structure, if the patient has to undergo magnetic resonance tomography or MRT.

There is still a need to provide a stent as defined above, the stent being highly expandable and having a high degree of flexibility at the same time. Furthermore, the stent must not disturb magnetic fields and thus the imaging of an MRT scan.

Thus, the invention relates to an implantable stent which can be used in the region of an arterial constriction said region being expandable by a balloon catheter. The stent is expandable and can be widened in a radial direction by virtue of the fact that the wall of the stent is formed at least in sections thereof from permanently deformable metal struts, whereby the stent consists of more than one tubular segment (10), wherein the segment (10) consist of metal struts (2) and wherein in each case two adjacent segments (10) are connected to each other by at least one pair of eyelets (6) and (7), where the eyelets (6) and (7) are connected to each other by being embedded in plastic and in this manner the segments (10) are held together, and where at least one of the metal struts (2) has a predetermined breaking point in the middle section of the segment (40), which predetermined breaking point is produced as a result of the fact that two strut sections (3) and (4) have eyelets (11), (12) respectively, which are connected to each other by being embedded in plastic, so that when they exceed a defined radial expansion, the metal struts (2) open as a result of the predetermined breaking point.

Benefits

The most important benefit of the highly flexible stent having a predetermined breaking point is that a surgery can be avoided later on for children with congenital pulmonary stenosis, aortic stenosis or other vascular diseases.

The high level of flexibility results from connecting the segments (10) via the eyelets (6) and (7) embedded in plastic.

If the vessels grow or change after implantation it is possible to stretch the stent again using a balloon. This option arises due to the connection of the metal struts through the eyelets (11) and (12) embedded in plastic, which form a predetermined breaking point.

The eyelets (11) and (12) made from non-conductive plastic ensure that the metallic wall of the stent is interrupted, so that no induction currents can form during an MRT scan thus disrupting the MRT imaging.

Another advantage of the eyelets embedded in plastic is that a reservoir can be created in the plastic to release drugs, thus creating a kind of drug-eluting stent.

The term "permanently deformable metal struts" means the stent remains in a permanently extended position in its extended state. The stent is extending in a radial direction transversely to the longitudinal axis of the metal struts.

The invention also relates to a stent as defined in claim 1 for use in a procedure to treat pulmonary stenosis or aortic isthmus stenosisin children.

DRAWINGS

Other details, features and benefits of the invention can be found in the description that follows, in which the invention is explained in more detail using drawings. The drawings show the following in a schematic presentation.

FIG. 1 is a representative example of the implantable stent.

FIG. 2 shows a part of the implantable stent in a two-dimensional format.

FIG. 3 is a detailed presentation of the eyelets embedded in plastic.

DESCRIPTION OF THE DRAWINGS

Segments (10) determine the radial expansion. Two strut sections (3) and (4) are present in the mid-segment section (40). The strut sections (3) and (4) each have eyelets (11, 12) which are connected to each other by being embedded in a non-conductive plastic. The segments are connected to each other by at least one pair of eyelets (6) and (7). These eyelets (6) and (7) are connected to each other by being embedded in plastic. FIG. 1 shows a version in which the segments (10) are connected to each other at two connecting points, formed by the eyelets (6) and (7).

Embedding in plastic may be the same for the eyelets (6) and (7) and for the eyelets (11) and (12) or different. For example, the eyelets (6) and (7) can be embedded in silicone and eyelets (11) and (12) in polyurethane. Having the same synthetic material is preferable.

The eyelets (6), (7) and (11) and (12) are each embedded next to each other in plastic. But it is also possible that when embedding them there is a space between the eyelets (6), (7) and between the eyelets (11) and (12).

Figure 1:
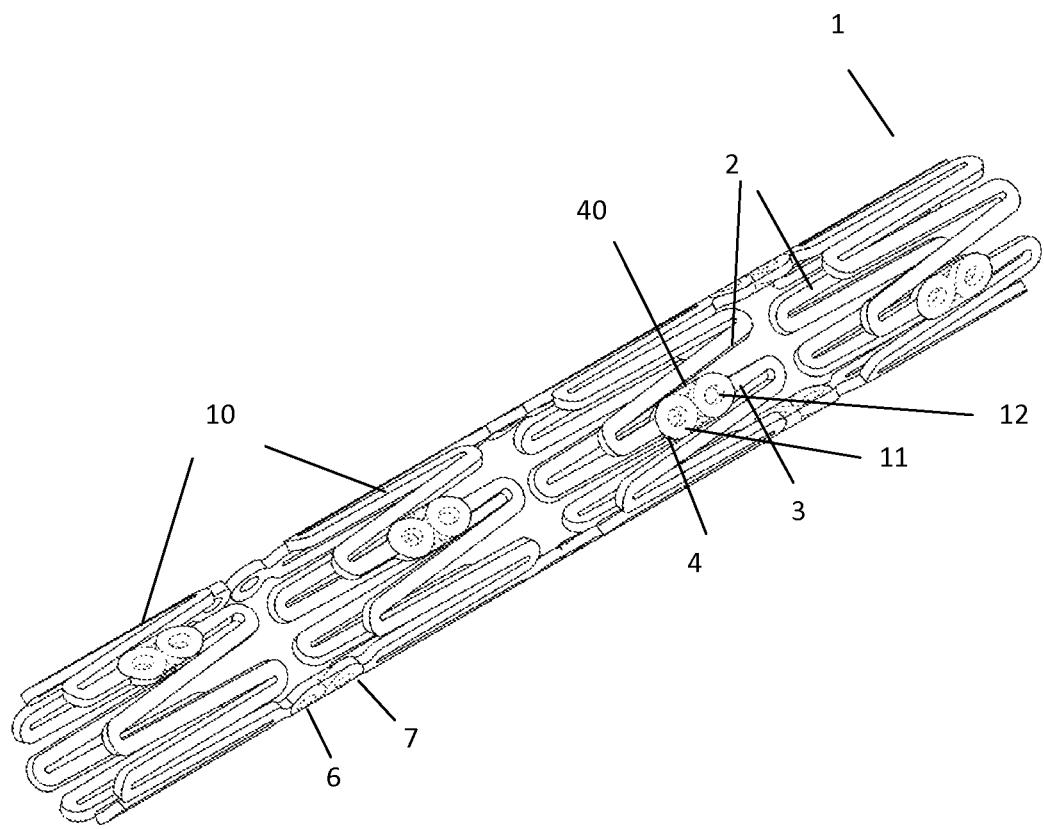
FIG. 1 is a representative example of the implantable stent (1). The stent consists of tubular segments (10). At least two segments must be present. The figure shows four segments (10). Normally the stent comprises 3-5 segments. The segments are made of metal struts (2). The stent's struts (2) are shaped in such a way to achieve the maximum possible expansion. The struts (2) are preferably sinusoidal and are made from stainless steel or nitinol, for example.
Figures 2, 3:
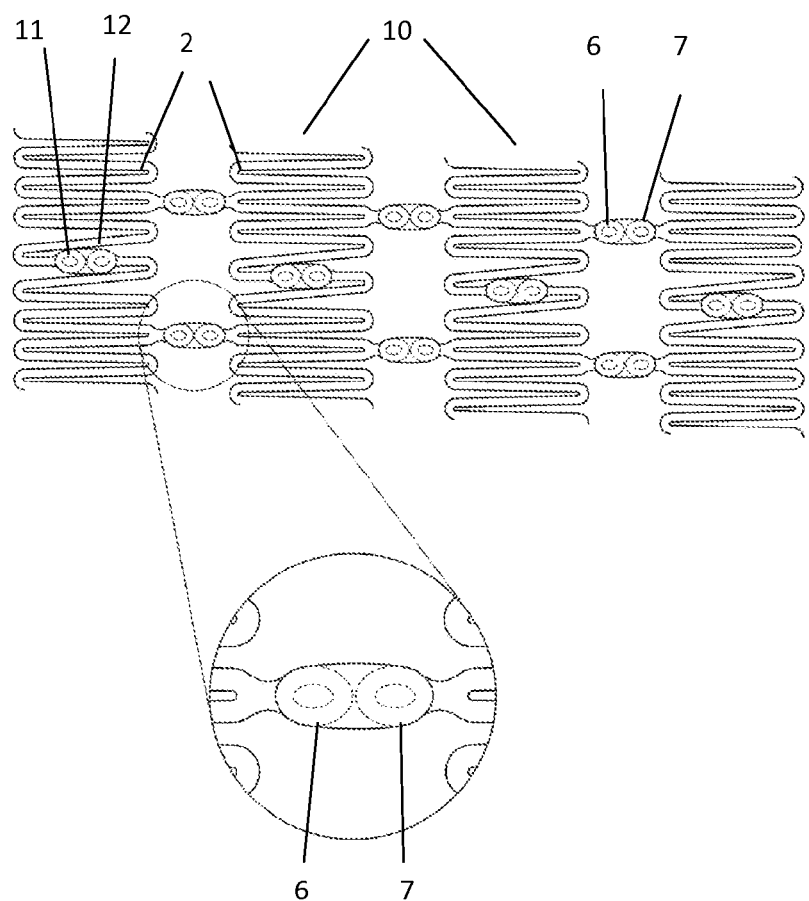
FIG. 2 shows a part of the implantable stent in a two-dimensional format. It is obvious that the eyelets (6) and (7) and the eyelets (11) and (12) are close together and are embedded in plastic. The dimensions and the material properties of the eyelets (11) and (12) and the plastic surrounding them determine essentially the desired predetermined breaking point. The dimensions and the material properties of the eyelets (6) and (7) and the plastic surrounding them determine essentially the desired flexibility of the individual segments (10). The eyelets (6), (7), (11) and (12) consist preferably of the same material as the struts (2). The plastic consists preferably of silicone or polyurethane and does not dissolve in the body. Silicone is especially preferred.

FIG. 3 is a magnified view of the eyelets (6), (7) embedded in plastic.

The invention claimed is:

1. Implantable stent, which can be used in the region of an arterial constriction, said region being expandable by a balloon catheter wherein the stent is expandable and can be widened in a radial direction by virtue of the fact that the wall of the stent is formed at least in sections thereof from permanently deformable metal struts, wherein the stent consists of more than one tubular segment, wherein the segment consist of metal struts and wherein in each case two adjacent segments are connected to each other by at least one pair of eyelets and, where the eyelets and are connected to each other by being embedded in silicone and in this manner the segments are held together, and where at least one of the metal struts has a predetermined breaking point in the middle section of the segment, which predetermined breaking point is produced as a result of the fact that two strut sections have eyelets, respectively, which are connected to each other by being embedded in silicone, so that when they exceed a defined radial expansion, the metal struts open as a result of the predetermined breaking point.

2. The stent according to claim 1, wherein there is a space between the eyelets when embedded.

3. The stent according to claim 1, wherein the silicone connection between the eyelets contains drugs.

* * * * *